United States Patent [19]

Imai

[11] 4,219,684

[45] Aug. 26, 1980

[54] SYNTHESIS OF ALCOHOLS BY HYDROFORMYLATION WITH NITRILE PROMOTER

[75] Inventor: Tamotsu Imai, Mt. Prospect, Ill.

[73] Assignee: UOP Inc., Des Plaines, Ill.

[21] Appl. No.: 26,477

[22] Filed: Apr. 2, 1979

[51] Int. Cl.$^2$ .............................................. C07C 29/00
[52] U.S. Cl. ................................................... 568/909
[58] Field of Search ........................................ 568/909

[56] References Cited

U.S. PATENT DOCUMENTS

| | | | |
|---|---|---|---|
| 3,527,809 | 9/1970 | Pruett et al. | 568/909 |
| 3,627,843 | 12/1971 | Pregaglia | 568/909 |
| 3,933,919 | 1/1976 | Wilkinson | 568/909 |
| 3,984,478 | 10/1976 | Homeier | 568/909 |
| 4,072,720 | 2/1978 | Haag et al. | 568/909 |

*Primary Examiner*—Joseph E. Evans
*Attorney, Agent, or Firm*—James R. Hoaston, Jr.; Raymond H. Nelson; William H. Page, II

[57] ABSTRACT

Alcohols may be synthesized by reacting an olefinic compound, carbon monoxide and hydrogen in the presence of a Group VIII organometallic complex catalyst at reaction conditions which include a temperature in the range of from about 50° to about 250° C. and a pressure in the range of from about 10 to about 300 atmospheres. In addition, the reaction is also effected in the presence of a promoter compound comprising a nitrile.

10 Claims, No Drawings

SYNTHESIS OF ALCOHOLS BY HYDROFORMYLATION WITH NITRILE PROMOTER

This invention relates to a process for the synthesis of alcohols. More specifically, the invention is concerned with a process for synthesizing alcohols, and specifically primary alcohols, by reacting olefinic hydrocarbons, carbon monoxide and hydrogen in the presence of certain catalytic compositions of matter as well as promoter compounds.

It is well known in the chemical art that alcohols constitute an important class of compounds. For example, relatively long chain primary alcohols such as n-dodecanol (lauryl alcohol) is an important intermediate in the preparation of synthetic detergents as well as lube additives, pharmaceuticals, rubber, textiles and perfumes. Likewise, n-tetradecanol (myristyl alcohol) is a useful intermediate in the preparation of plasticizers as well as being used as an antifoam agent, an intermediate in the preparation of perfume fixitives for soaps and cosmetics, as well as being a base for the manufacture of wetting agents and detergents, while n-hexadecanol (cetyl alcohol) is used as an intermediate for the preparation of compounds useful in medicines, perfumes, emulsifiers, cosmetics, etc. Lower molecular weight alcohols such as butanol is utilized by the preparation of esters such as butyl acetate, as a solvent for resins and coatings, as well as being used in plasticizers, detergent formulations, dehydrating agents, hydraulic fluids, etc.

It is therefore an object of this invention to provide a process for the synthesis of alcohols.

A further object of this invention is to provide a process for synthesizing alcohols utilizing relatively inexpensive starting materials, said process being effective in the presence of certain catalysts and also in the presence of a nitrile promoter.

In one aspect an embodiment of this invention resides in a process for the production of an alcohol which comprises reacting an organic compound, carbon monoxide and hydrogen in the presence of a Group VIII organometallic complex catalyst and a nitrile promoter at reaction conditions, and recovering the resultant alcohol.

A specific embodiment of this invention is found in a process for the synthesis of an alcohol which comprises reacting undecene, carbon monoxide and hydrogen in the presence of chlorodicarbonylrhodium dimer and succinonitrile at a temperature in the range of from about 50° to about 250° C. and a pressure in the range of from about 10 to about 300 atmospheres, and recovering the resultant dodecanol.

Other objects and embodiments will be found in the following further detailed description of the present invention.

As hereinbefore set forth, the present invention is concerned with a process for the synthesis of alcohols in which an olefinic hydrocarbon is reacted with carbon monoxide and hydrogen in the presence of certain catalytic compositions of matter and a nitrile promoter. The reaction conditions which are employed to produce the desired results will include a temperature in the range of from about 50° to about 250° C. and pressures within the range of from about 10 to about 300 atmospheres. In the preferred embodiment of the invention the pressures which are employed to effect the desired result will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.1:1 to about 5:1 moles of hydrogen per mole of carbon monoxide.

Examples of olefinic hydrocarbons which may be employed to effect the process of this invention will include straight chain and branched chain olefins containing from 2 to about 30 carbon atoms such as propylene, butene-1, butene-2, pentene-1, pentene-2, 2-methylbutane-1, hexene-1, hexene-2, hexene-3, 2-methylpentene-1, 3-methylpentene-1, heptene-1, heptene-2, heptene-3, octene-1, octene-2, 2-methylheptene-1, 3-methylheptene-1, 3-methylheptene-2, octene-3, octene-4, nonene-1, nonene-2, nonene-3, nonene-4, as well as the isomeric decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, cyclopentene, cyclohexene, cycloheptene, styrene, etc.; dienes such as 1,3-butadiene, 1,3-pentadiene, 1,3-hexadiene, 2,4-hexadiene, 1,3-heptadiene, 2,4-heptadiene, etc.

The reaction between the olefinic hydrocarbons of the type hereinbefore set forth, carbon monoxide and hydrogen is effected in the presence of a catalyst comprising a Group VIII organometallic complex. In the preferred embodiment the metallic portion of the catalyst will be selected from rhodium and ruthenium, representative examples of these rhodium- and ruthenium-containing compounds comprising the metals, nitrates, halides, halocarbonyls, organometallic complexes, oxides or carbonyl complexes. Specific examples of these compounds which are employed will include rhodium, rhodium nitrate, rhodium chloride, rhodium bromide, rhodium iodide, rhodium fluoride, rhodium acetate dimer, rhodium oxide, chlorodicarbonylrhodium dimer, rhodium carbonyl, chlorobis(ethylene)rhodium dimer, hexarhodiumhexadecylcarbonyl, tetrahodiumdodecylcarbonyl, chlororhodiumcarbonyl dimer, hydridorhodiumtris(trimethylphosphene)carbonyl, hydridorhodiumtris(tri-n-butylphosphene)carbonyl, hydridorhodiumtris(triphenylphosphene)carbonyl, hydridorhodiumtris(trimethylphosphite)carbonyl, hydridorhodiumtris(triethylphosphite)carbonyl, hydridorhodiumtris(triphenylphosphite)carbonyl, rhodium acetylacetonate, ruthenium, ruthenium nitrate, ruthenium chloride, ruthenium bromide, ruthenium iodide, ruthenium fluoride, dichlorotricarbonylruthenium, rutheniumcarbonyl, etc. It is to be understood that the aforementioned organometallic complexes are only representative of the class of compounds which may be employed, and that the present invention is not necessarily limited thereto.

In addition to utilizing the catalyst of the type hereinbefore set forth in greater detail, the reaction between the olefinic compound, carbon monoxide and hydrogen is effected in the presence of a nitrile compound. The nitrile compounds can include alkyl nitriles, alkyl dinitriles, alkenyl nitriles, and aromatic nitriles. Specific examples of these compounds which may be employed will include acetonitrile (methyl cyanide), propionitrile (ethyl cyanide), butyronitrile (propyl cyanide), valeronitrile (butyl cyanide), capronitrile (amyl cyanide), enanthylonitrile (hexyl cyanide), caprylonitrile (heptyl cyanide), octyl cyanide, nonyl cyanide, decyl cyanide, undecyl cyanide, dodecyl cyanide, tridecyl cyanide, etc.; dinitriles such as oxalonitrile, malononitrile, succinonitrile, glutaronitrile, adiponitrile, pimelonitrile, suberonitrile, axelonitrile, etc.; alkenyl nitriles such as acrylonitrile, crotononitrile, isocrotononitrile, tiglonitrile and angelonitrile, etc.; aromatic nitriles such as benzonitrile, 2-methylbenzonitrile, 3-methylbenzonitrile, 4-methylbenzonitrile, etc.; substituted nitriles such as dimethylacetonitrile, diethylacetonitrile, diphenylacetonitrile, dimethylpropionitrile, diethylpropionitrile, diphenylpropionitrile, dimethylbutyronitrile, diethylbutyronitrile, diphenylbutyronitrile, dimethylsuccinonitrile, diethylsuccinonitrile, diphenylsuccinonitrile, etc. It is to be understood that the aforementioned nitrile compounds are only representative of the class of compounds which may be employed as promoters, and that the present invention is not necessarily limited thereto.

The process of this invention may be effected in any suitable manner and may comprise either a batch or continuous type of operation. When a batch type of operation is used, a quantity of the olefinic hydrocarbon, the Group VIII organometallic complex catalyst and the nitrile promoter are placed in an appropriate pressure resistant apparatus such as an autoclave of the rotating, rocking or mixing type. After placing the components of the reaction in the autoclave, it is then sealed and hydrogen and carbon monoxide are charged thereto until the desired operating pressure has been attained. Alternatively, as hereinbefore discussed, if higher pressures are to be employed a portion of the pressure may be afforded by the introduction of a substantially inert gas into the reaction zone. After reaching the proper operating pressure, the apparatus is then heated to the desired operating temperature which may range from about 50° to about 250° C. and maintained thereat for a predetermined residence time which may range from about 0.5 hours up to about 10 hours or more in duration. Upon completion of the desired residence time, heating is discontinued and the apparatus and contents thereof are allowed to return to room temperature. Upon reaching room temperature the pressure is discharged, the apparatus is opened, and the reaction mixture is recovered therefrom. After separation from the catalyst, the reaction mixture may be subjected to conventional means of separation whereby the desired alcohol is separated from any unreacted starting material, promoter and/or unwanted side reaction products which may have formed and recovered. A particular advantage which may be obtained when utilizing the process of the present invention is that the catalysts which are employed to effect the reaction are easily recovered as distillation bottom products and may be recycled for reuse. In addition another advantage which is present is that the loss of products in the distillation step is relatively low inasmuch as alcohols do not polymerize readily and may therefore be recovered in an excellent yield.

It is also contemplated within the scope of this invention that the synthesis of alcohols may be accomplished by utilizing a continuous method of operation. When utilizing this type of operation, the olefinic hydrocarbon is continuously charged to a reaction zone which is maintained at the proper operating conditions of temperature and pressure and which contains a catalyst of the type hereinbefore set forth as well as the nitrile promoter. Alternatively, the nitrile promoter may also be continuously charged to the reaction zone either separately or along with the olefinic hydrocarbon charge. In addition to the continuous charging of the reactant to the operating zone, hydrogen and carbon monoxide either separately or in admixture are also charged thereto. Upon completion of the desired residence time in the reaction zone, the reactor effluent is continuously withdrawn and subjected to conventional means of separation, such as fractional distillation, whereby the desired alcohol is separated from unreacted starting materials and/or undesired side reaction products which may have formed, and recovered, while the unreacted starting materials may be recycled to the reaction zone to form a portion of the feed stock.

Examples of alcohols which may be synthesized according to the process of the present invention will include primary alcohols such as ethanol, propanol, butanol, pentanol, 2-methyl-1-butanol, hexanol, 3-methyl-1-pentanol, heptanol, 3-methyl-1-hexanol, octanol, nonanol, decanol, 2-methyl-1-nonanol, undecanol, dodecanol, 3-methyl-1-undecanol, tridecanol, tetradecanol, pentadecanol, hexadecanol, heptadecanol, octadecanol, nonadecanol, eicosanol, 2-phenyl-1-ethanol, cyclohexanol, cycloheptanol, etc. It is to be understood that the aforementioned alcohols are only representative of the compounds which may be synthesized, and that the present invention is not necessarily limited thereto.

The following examples are given to illustrate the process of the present invention. However, it is to be understood that these examples are given merely for purposes of illustration and that the present invention is not necessarily limited thereto.

EXAMPLE I

As an illustration of the need for a promoter comprising a nitrile compound, an experiment was performed in which 0.0283 gram of a catalyst comprising chlorodicarbonylrhodium dimer was placed in the glass liner of an 850 cc rocking autoclave. Thereafter 26.42 grams of undecene was placed in the autoclave, the autoclave was sealed and a 1:1 mole ratio mixture of carbon monoxide and hydrogen was charged to the autoclave until 150 atmospheres of the blend gas had been added. The autoclave was then heated to a temperature of 150° C. and maintained thereat for a period of 3 hours. During this time period the pressure in the autoclave fell from 181 atmospheres to 158 atmospheres. At the end of the 3 hour period, heating was discontinued and the autoclave was allowed to return to room temperature. Upon reaching room temperature the excess pressure was discharged, the autoclave was opened and the reaction mixture was recovered. Analysis of the product by means of gas liquid chromatography disclosed that there had been a 100% conversion of the undecene with a product selectivity comprising 20% dodecanol and 76% dodecanal.

EXAMPLE II

In this example 0.0315 gram of chlorodicarbonylrhodium dimer and 26.53 grams of undecene along with 1.83 grams of succinonitrile were placed in the glass liner of a rocking autoclave, the molar ratio of succinonitrile to rhodium being 146:1. The autoclave was sealed and a blend gas comprising a 1:1 mole ratio of carbon monoxide and hydrogen was charged thereto until a pressure of 150 atmospheres was reached. The autoclave was heated to a temperature of 150° C. being maintained at that temperature for a period of 3 hours, the pressure during this time dropping from 165 to 158 atmospheres. At the end of the 3 hour period heating was discontinued and after the autoclave had returned to room temperature, the excess pressure was discharged. After recovery of the reaction mixture, it was subjected to gas liquid chromatography which disclosed that there had been a 100% conversion of the undecene. In contradistinction to the previous experiment in which no nitrile was present as a promoter, the product selectivities rose to an 81% selectivity of dodecanol with only a 16% product selectivity to dodecanal.

EXAMPLE III

The experiment described in Example II above was repeated using 0.0262 gram of chlorodicarbonylrhodium dimer, 26.5 grams of undecene and 2.42 grams of adiponitrile. After sealing the autoclave, a blend gas comprising a 1:1 mole ratio of carbon monoxide and hydrogen was charged to the autoclave until an initial operating pressure of 150 atmospheres was reached. The autoclave was then heated to a temperature of 150° C. and maintained thereat for a period of 3 hours, the pressure during this time dropping from 199 atmospheres to 180 atmospheres. After discontinuing the heating and allowing the autoclave to return to room temperature, the excess pressure was discharged and the reaction mixture was recovered. Gas liquid chromatographic analysis of the reaction product determined that there had been a 100% conversion of the undecene, the produce containing a 78% selectivity to dodecanol and a 15% product selectivity to dodecanal.

When the above experiment was repeated using benzonitrile, diphenylacetonitrile, and acetonitrile as the promoting agents, it was determined by analysis that in each instance there had been a 100% conversion of the undecene while the product selectivity to dodecanol comprised 56%, 44% and 25% respectively, the product selectivity to aldehydes being 41%, 51.5% and 72% respectively.

EXAMPLE IV

To determine an optimum mole feed ratio of nitrile to the metallic portion of the catalyst, a series of experiments were performed in which the molar ratio of nitrile to rhodium varied from 0:1 to 505:1. As in the previous experiments, all runs were made at a temperature of 150° C. using chlorodicarbonylrhodium dimer as the catalyst, succinonitrile as the nitrile promoter and 150 atmospheres of a 1:1 carbon monoxide:hydrogen blend gas. The runs were made during a period of 3 hours in a rocking autoclave. Gas liquid chromatographic analysis of the reaction product which is recovered at the end of this run determined that there had been a 100% conversion of the undecene in all instances. Table I below illustrates the effect of the varying mole ratio of nitrile promoter to rhodium catalyst.

TABLE I

| Nitrile/Rhodium | Product Selectivities, % | |
|---|---|---|
| Mole Ratio | Dodecanol | Dodecanal |
| 0 | 20 | 76 |

TABLE I-continued

| Nitrile/Rhodium | Product Selectivities, % | |
|---|---|---|
| Mole Ratio | Dodecanol | Dodecanal |
| 16 | 64 | 31 |
| 144 | 81 | 16 |
| 229 | 81 | 16 |
| 505 | 86 | 9 |

EXAMPLE V

In this example a series of runs were performed to illustrate the effect of temperature with and without the presence of a nitrile modifier. As in the previous experiments, about 26.5 grams of undecene were reacted in the presence of a chlorodicarbonylrhodium dimer catalyst which is present in an amount of about 0.027 gram. In each instance the runs were performed under 200 atmospheres of a 1:1 carbon monoxide/hydrogen blend gas for a period of 3 hours in an autoclave, the temperature varying from 150° to 200° C. Two of the runs were made in the absence of a nitrile modifier while two runs were made in the presence of about 2 grams of succinonitrile. The results of these runs are set forth in Table II below.

TABLE II

| Nitrile/Rhodium Molar Ratio | Reactor Temp. °C. | Undecene Conversion, % | Product Selectivities | |
|---|---|---|---|---|
| | | | Dodecanol | Dodecanol |
| 0 | 150 | 100 | 20 | 76 |
| 0 | 200 | 91 | 8 | 85 |
| 229 | 150 | 100 | 81 | 16 |
| 163 | 200 | 98 | 94 | 1 |

It is therefore readily apparent from a review of this table that the presence of a nitrile modifier in the reaction system contributed greatly to an increase in the production of alcohols from undecene as compared to the production of aldehydes.

EXAMPLE VI

In a manner similar to that set forth in the above examples, a catalyst comprising rhodium chloride may be placed in a rotating autoclave along with a charge stock comprising a mixture of octenes. A promoter compound comprising adiponitrile in an amount sufficient to maintain an adiponitrile/rhodium molar ratio of 171:1 may also be placed in the autoclave which is thereafter sealed. A blend gas comprising a 1:1 mole ratio of carbon monoxide and hydrogen may also be charged to the sealed autoclave until an initial operating pressure of 150 atmospheres is reached. Thereafter the autoclave may be heated to a temperature of 200° C. and maintained thereat for a period of 3 hours, at the end of which time heating may be discontinued and the autoclave allowed to return to room temperature. After returning to room temperature the excess pressure may be discharged and the autoclave opened. The reaction mixture may then be subjected to gas liquid chromatographic analysis to determined the conversion of the octenes and the obtention of nonanol in a relatively high product selectivity.

Similar experiments using heptene, docosene and butene as a charge stock for reaction with carbon monoxide and hydrogen in the presence of a rhodium, ruthenium or cobalt containing organometallic complex and in the presence of various nitrile promoters such as benzonitrile may also result in obtaining the corresponding alcohols, namely, octanol, tricosanol, and butanol, and relatively high percentages of product selectivities.

I claim as my invention:

1. A process for the production of an alcohol which comprises reacting an olefinic compound, carbon monoxide and hydrogen in the presence of a chlorodicarbonylrhodium dimer catalyst and a nitrile promoter at reaction conditions, and recovering the resultant alcohol.

2. The process as set forth in claim 1 in which said reaction conditions include a temperature in the range of from about 50° to about 250° C. and a pressure in the range of from about 10 to about 300 atmospheres.

3. The process as set forth in claim 1 in which said nitrile promoter is succinonitrile.

4. The process as set forth in claim 1 in which said nitrile promoter is adiponitrile.

5. The process as set forth in claim 1 in which said nitrile promoter is benzonitrile.

6. The process as set forth in claim 1 in which said olefinic compound is undecene and said alcohol is dodecanol.

7. The process as set forth in claim 1 in which said olefinic compound is octene and said alcohol is nonanol.

8. The process as set forth in claim 1 in which said olefinic compound is heptene and said alcohol is octanol.

9. The process as set forth in claim 1 in which said olefinic compound is docosene and said alcohol is tricosanol.

10. The process as set forth in claim 1 in which said olefinic compound is butene and said alcohol is pentanol.

* * * * *